US012029925B2

(12) United States Patent
Vincenot et al.

(10) Patent No.: US 12,029,925 B2
(45) Date of Patent: Jul. 9, 2024

(54) ULTRASOUND PRODUCTION SOURCE WITH AN OUTSIDE THREAD

(71) Applicant: EDAP TMS FRANCE, Vaulx-en-Velin (FR)

(72) Inventors: Jérémy Vincenot, Villeurbanne (FR); Olivier Nallet, Lyons (FR); David Nury, Bourgoin Jallieu (FR)

(73) Assignee: EDAP TMS FRANCE, Vaulx-en-Velin (FR)

( * ) Notice: Subject to any disclaimer, the term of this patent is extended or adjusted under 35 U.S.C. 154(b) by 277 days.

(21) Appl. No.: 16/261,994

(22) Filed: Jan. 30, 2019

(65) Prior Publication Data

US 2019/0247679 A1 Aug. 15, 2019

(30) Foreign Application Priority Data

Feb. 12, 2018 (FR) ...................................... 18 51140

(51) Int. Cl.
 *A61N 7/02* (2006.01)
 *A61B 8/00* (2006.01)
 *A61B 17/225* (2006.01)

(52) U.S. Cl.
 CPC .............. *A61N 7/02* (2013.01); *A61B 8/4411* (2013.01); *A61B 8/4444* (2013.01); *A61B 8/58* (2013.01);
(Continued)

(58) Field of Classification Search
 CPC ...... A61N 2007/0052; A61N 7/02–022; A61N 2007/025–027; A61B 8/58;
(Continued)

(56) References Cited

U.S. PATENT DOCUMENTS 2,490,236 A * 12/1949 Shaper ..................... B06B 1/06
 310/337
4,936,303 A * 6/1990 Detwiler .................. A61N 7/02
 601/3
(Continued)

FOREIGN PATENT DOCUMENTS

CN 2118536 U * 10/1992
JP 2005053527 A * 3/2005
JP 2009067458 A * 4/2009

OTHER PUBLICATIONS

Wikipedia, Bonded Seal, modified Dec. 27, 2016, accessed Jan. 27, 2021, https://en.wikipedia.org/wiki/Bonded_seal. (Year : 2016).*
(Continued)

*Primary Examiner* — Keith M Raymond
*Assistant Examiner* — Patrick M Mehl
(74) *Attorney, Agent, or Firm* — LADAS & PARRY LLP; Malcolm J. MacDonald, Esq.

(57) ABSTRACT

The invention provides an ultrasound production source comprising a body containing an ultrasound transducer presenting in front an emission face, the body including an opening (5) defined by a tubular wall (6) and arranged so that the emission face of the ultrasound transducer faces towards the opening (5), the tubular wall (6) being provided externally with at least one thread (17) of a screw thread assembly system for co-operating with at least one complementary thread (16) either of a fastener ring (15) for fastening a flexible membrane (8) on the body, or of a protective cover, or of a ring fitted with an alignment system.

9 Claims, 6 Drawing Sheets

(52) U.S. Cl.
CPC ... *A61B 17/2251* (2013.01); *A61B 2017/2253* (2013.01)

(58) Field of Classification Search
CPC ..... A61B 8/4411; A61B 8/546; A61B 8/4444; A61B 8/14; A61B 17/2251; A61B 2017/2253; A61B 17/22004; A61B 2017/22005–22011; A61B 17/22022; A61B 2017/22024–22025; A61B 17/225–2258; A61B 5/58; B06B 1/02; B06B 1/06

See application file for complete search history.

(56) References Cited

U.S. PATENT DOCUMENTS

| | | | | |
|---|---|---|---|---|
| 5,827,204 | A * | 10/1998 | Grandia | A61B 17/2256 601/2 |
| 6,261,231 | B1 * | 7/2001 | Damphousse | A61B 8/4209 600/437 |
| 2004/0050163 | A1 * | 3/2004 | Komninos | G01N 29/4427 73/587 |
| 2004/0097840 | A1 | 5/2004 | Holmer | |
| 2007/0199391 | A1 * | 8/2007 | Fourqurean | F04B 1/02 74/25 |
| 2013/0131704 | A1 | 5/2013 | Pechoux | |
| 2014/0188011 | A1 * | 7/2014 | Wurster | A61N 7/00 601/2 |
| 2014/0378874 | A1 * | 12/2014 | Wurster | A61N 7/00 601/2 |
| 2015/0182200 | A1 | 7/2015 | Birglehner et al. | |

OTHER PUBLICATIONS

Amazon, Neoprene EPDM Bonded Sealing Washers Stainless Steel 18-8, available Mar. 2, 2015, accessed Jan. 27, 2021, https://www.amazon.com/Neoprene-Bonded-Sealing-Washers-Stainless/dp/B00YG5QQ0l?th=1. (Year: 2015).*

Wikipedia, Washer (hardware), modified Sep. 19, 2017, accessed Jan. 28, 2021, https://en.wikipedia.org/wiki/Washer_(hardware). (Year: 2017).*

Neoprene EPDM Bonded Sealing Washers Stainless Steel 18-8, Amazon, available Mar. 2, 2015, accessed Jan. 27, 2021, https://www.amazon.com/Neoprene-Bonded-Sealing-Washers-Stainless/dp/B00YG5QQ0l?th=1. (Year: 2015).*

Bonded Seal, Wikipedia, Wikimedia Foundation, modified Dec. 27, 2016, accessed Jan. 27, 2021, https://en.wikipedia.org/wiki/Bonded_seal. (Year: 2016).*

Washer (hardware), Wikipedia, Wikimedia, modified Sep. 19, 2017, accessed Jan. 28, 2021, https://en.wikipedia.org/wiki/Washer_(hardware). (Year: 2017).*

* cited by examiner

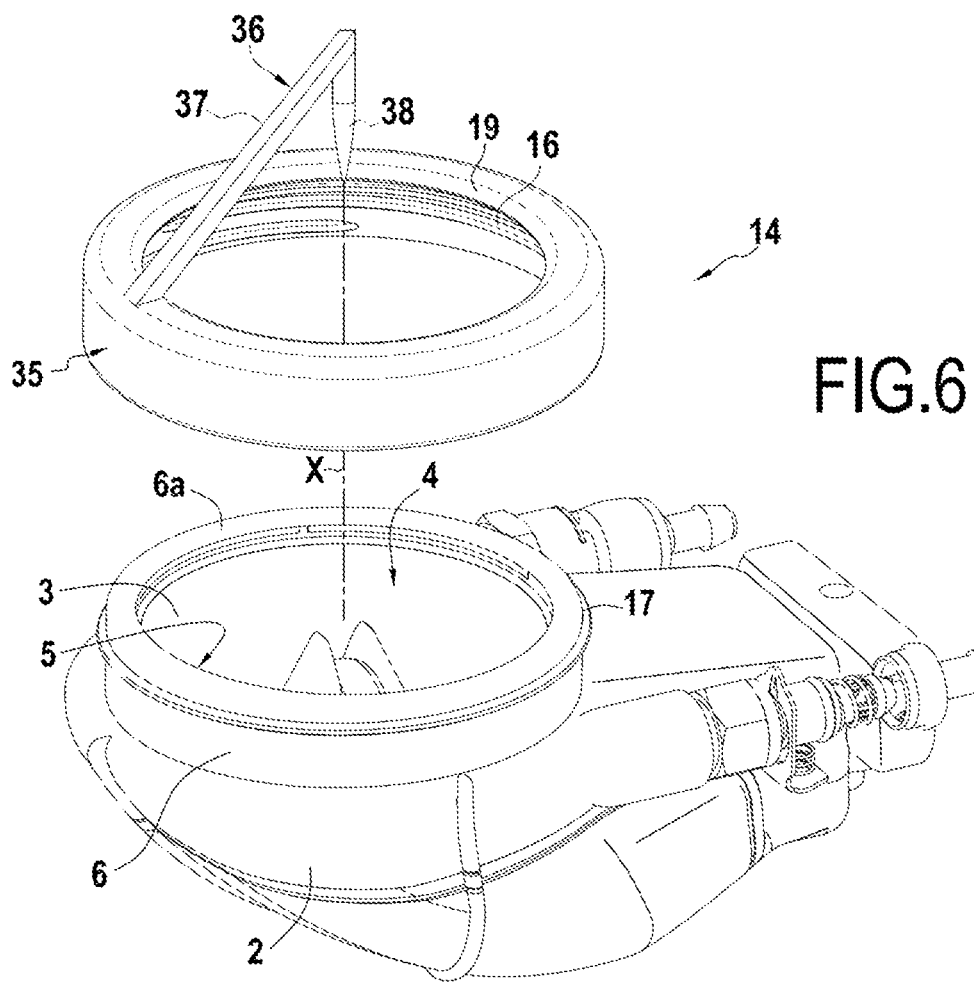

ULTRASOUND PRODUCTION SOURCE WITH AN OUTSIDE THREAD

The present invention relates to the technical field of apparatuses or devices including a source for producing ultrasonic waves and for use in the field of therapy, and possibly being associated with an ultrasound probe for echographic imaging of human anatomy.

The invention thus finds a particularly advantageous application in the field of therapeutic appliances including a source for producing high intensity focused ultrasound (HIFU).

The invention finds another particularly advantageous application in the field of appliances for destroying solid intracorporeal concretions for treating lithotrity, comprising a source for producing ultrasonic pressure waves such as acoustic shock waves that serve to destroy renal, bile, or salivary concretions or calculi.

In general manner, a source for producing ultrasound comprises a mounting body for mounting an acoustic transducer that converts electrical energy into mechanical energy. Towards its front, the ultrasound transducer presents an emission face that co-operates with a flexible membrane to define a confinement chamber for confining an acoustic coupling and/or cooling fluid. Conventionally, the flexible membrane is mounted on an annular support of the body by using a fastener system of leaktight and releasable nature so that it can be replaced after each use.

Typically, the flexible membrane is mounted on the annular support by means of an elastic ring exerting a return force that is adapted to be sufficient to ensure that the membrane is mounted in leaktight manner on the support, while still enabling the ring to be put into place manually while exerting a force that enables the ring to be installed easily. In practice, the operation of mounting the flexible membrane is found to be relatively difficult to carry through so as to ensure good sealing of the confinement chamber all around the periphery of the annular support. In addition, that mounting operation sometimes leads to the ultrasound transducer being destroyed by the operator inadvertently by applying pressure, given the difficulty of putting the elastic ring into place.

Patent application EP 2 327 450 describes a probe for producing ultrasound that includes a removable flexible membrane that is to cover a HIFU head in which a HIFU transducer is mounted. The probe is provided with connection means to provide releasable fastening between the membrane and the HIFU head. Those connection means include a circumferential groove made on the inside of the membrane that can be engaged with a circumferential rib formed on the outside of the HIFU head. Additionally, the membrane includes three peripheral ribs on its inside face for pressing against the HIFU head in order to provide sealing and a flow path for the cooling liquid that is confined between the membrane and the HIFU head.

It should be observed that the operation of mounting the flexible membrane requires the membrane to be deformed elastically in order to engage the groove on the rib of the head. Even if the membrane has a pull tab, putting it into place so as to ensure good sealing around the entire periphery of the HIFU head requires the application of a non-negligible manual force that it is difficult to control.

In the field of echographic probes, Document US 2015/0182200 describes an echographic probe having a probe head connected by a cable to a connector having a cooling system for causing a cooling fluid to circulate between the probe head and the connector. The cooling system includes a damper for damping the fluid pressure pulses that are created by the pump and which are harmful for the quality of ultrasound images. That vibration damper comprises a flexible membrane mounted to define on one side a cooling fluid reception chamber and on its other side a closed air chamber. Sealing between the two chambers is provided by compressing the membrane, which is sandwiched between the housing and a ring screwed onto the inside of the housing. The pulses of the cooling fluid are absorbed by mechanically deforming the flexible membrane.

That document is silent concerning a description of the head of the probe and concerning a mounting device, if any, for mounting a removable membrane defining a confinement chamber for confining the cooling fluid relative to the ultrasound transducer.

An analysis of the prior art reveals that there is a need to be able to have an ultrasound probe that is adapted to be capable of being fitted with a flexible membrane without having recourse to tools and without it being necessary to perform manipulations that are difficult to carry through. Additionally, the ultrasound transducer that is placed in the proximity of the opening of the housing that receives the membrane runs the risk of being damaged while the membrane is being put into place, and also while the ultrasound probe is not in use. There is therefore also a need to be able to protect the ultrasound transducer of the probe, both while it is in use and also during periods when it is not in use, by means of a system that is effective and simple to put into place.

It should be observed that the ultrasound probe is subjected to calibration operations that require an alignment system to be used for aligning the ultrasound beam. In addition to the problems of positioning such an alignment system relative to the ultrasound beam, that calibration operation needs to be carried through without any risk of damaging the ultrasound transducer.

The present invention seeks to remedy the drawbacks of the prior art by proposing a novel source for producing ultrasound that is designed to optimize the various actions that need to be taken while it is in use.

An object of the present invention is to propose a novel source for producing ultrasound that is designed to make the following operations easier without risk of damaging the ultrasound transmitter:
  installing the flexible membrane for confining the acoustic coupling and/or cooling fluid;
  protecting the ultrasound transducer while the probe is not in use; and
  calibrating the ultrasound transducer.

In order to achieve these objects, the ultrasound production source of the invention comprises a body containing an ultrasound transducer presenting in front an emission face, the body including an opening defined by a tubular wall and arranged so that the emission face of the ultrasound transducer faces towards the opening, the tubular wall being provided externally with at least one thread of a screw thread assembly system for co-operating with at least one complementary thread either of a fastener ring for fastening a flexible membrane on the body, or of a protective cover, or of a ring fitted with an alignment system.

In an embodiment of the invention in which the source is used for producing ultrasound, the source needs to be fitted with a flexible membrane in order to confine an acoustic coupling and/or cooling fluid. In this embodiment, the probe of the invention includes a fastener ring possessing a central passage for passing a portion of the flexible membrane, the fastener ring, when screwed onto the body, serving to hold the flexible membrane pressed in sealed manner against the body.

In this embodiment, the tubular wall of the body is provided at its end with an annular rim against which the flexible membrane bears.

In an advantageous variant embodiment, the fastener ring is provided with a washer mounted to turn freely relative to the fastener ring so as to avoid being turned while screwing on the fastener ring, the washer exerting a pressure force on the flexible membrane when the fastener ring is screwed in position on the body. Such a device serves to mount the membrane on the housing without creases.

Furthermore, the ultrasound production source of the invention may also include, in combination, one or more of the following additional characteristics:

the washer is mounted in the fastener ring with limited freedom to move laterally in order to exert a pressure force on the flexible membrane when the fastener ring is screwed in position on the body;
the washer is held in the fastener ring inside an annular recess of C-shaped section;
a sealing gasket in contact with the flexible membrane;
the washer is fitted with the sealing gasket;
the washer is made of polytetrafluoroethylene; and
the thread or the complementary thread may be made in the form of a continuous element or in the form of discontinuous elements such as studs.

In another embodiment of the invention, in which the ultrasound transducer is to be protected, the body has a thread co-operating with a complementary thread of a protective cover.

In another embodiment of the invention, in which it is necessary to perform a stage of calibrating the ultrasound transducer, the body includes a thread co-operating with a complementary thread of an alignment system suitable for use in particular during the calibration step.

The present invention also proposes ultrasound treatment apparatus including an ultrasound production source in accordance with the invention.

Various other characteristics appear from the following description made with reference to the accompanying drawings which show embodiments of the invention as non-limiting examples.

FIG. 6 is an exploded perspective view showing an embodiment of an ultrasound production source in accordance with the invention or fitting with a ring having an alignment system.

Figure 1:
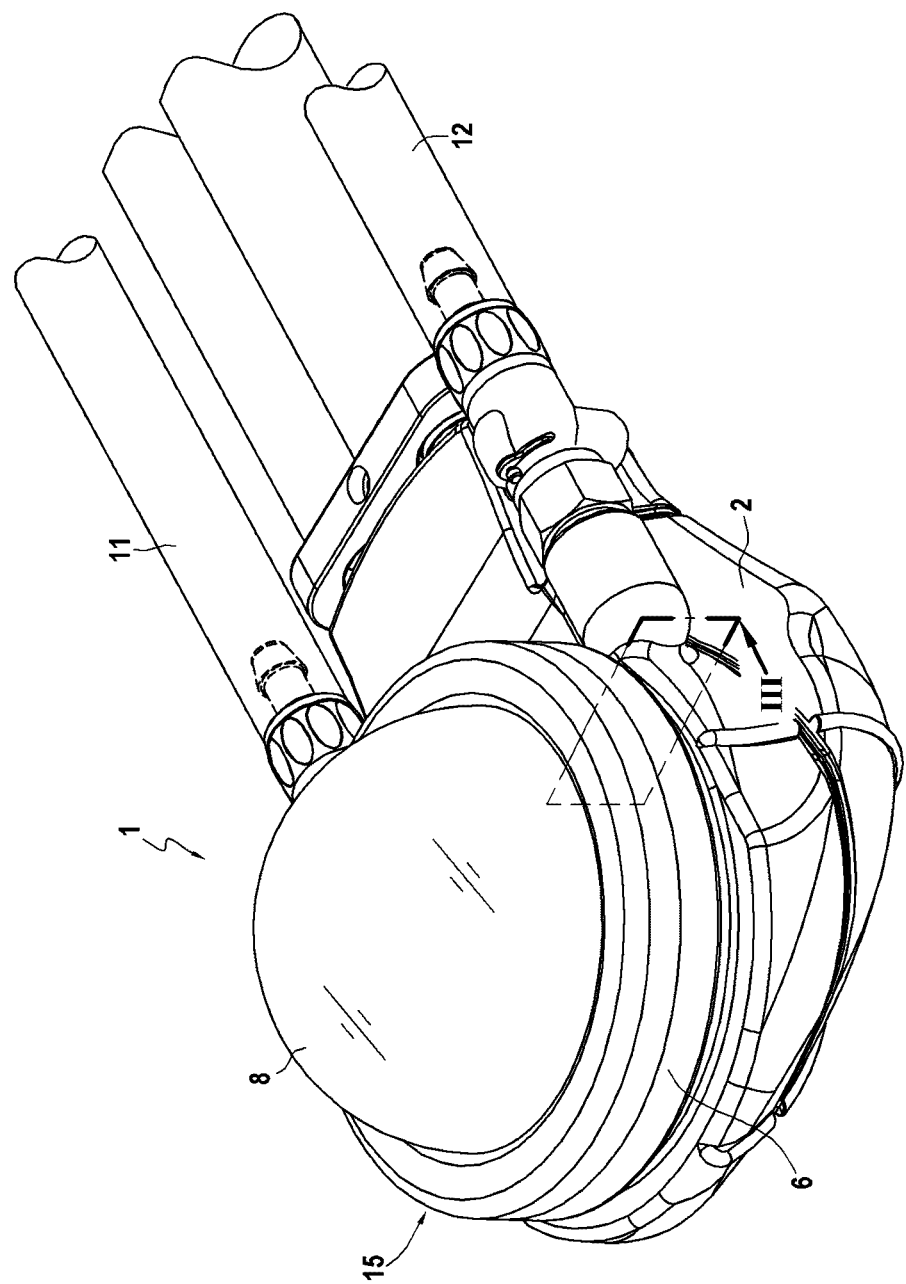
FIG. 1 is a perspective view of an embodiment of an ultrasound production source embodying the invention.

As can be seen from the drawings, the invention relates to a source 1 for producing ultrasound for thermal treatment of biological tissues. The source 1, which is used more particularly for therapeutic treatment, forms part of apparatus for performing therapy in the general sense, which apparatus is not shown but is itself known and is suitable for performing treatment of the tissue of a living being by means of ultrasound. In an advantageous application, the therapy source produces high intensity focused ultrasound (HIFU). In another application, the source produces ultrasonic pressure waves such as acoustic shock waves. Naturally, this source producing therapeutic ultrasound may optionally be associated with a probe for echographic imaging of human anatomy.

The ultrasound production source 1 includes in particular a body 2 for supporting a transducer 3 having one or more ultrasound emitters, such as for example piezoelectric elements. The ultrasound emitters of the transducer 3 are connected via an amplifier stage to a control circuit that delivers signals for activating the ultrasound emitters. The control circuit is not described in greater detail since making such a circuit forms part of the technical knowledge of the person skilled in the art. The control circuit also conventionally includes a controlled signal generator that is connected to the ultrasound emitters via the amplifier stage.

At its front, the transducer 3 presents an ultrasound emission face 4 facing towards an opening 5 arranged in the body 2. Typically, the body 2 or housing is arranged to present a tubular wall 6 presenting a collar or neck. This tubular wall 6 of the body is defined between an outside face 6e and an inside face 6i, and it is provided at its end with an annular rim 6a defining the inside of the opening 5.

In general manner, the emission face 4 possesses an axis of symmetry X corresponding to the soundwave propagation axis passing substantially through the center of the opening 5. In an advantageous variant embodiment, the emission face 4 presents a focusing shape, i.e. the ultrasound that is produced is focused in a focal zone either because of the way in which the ultrasound emitters are controlled or else because of the geometrical shape of the emission face. Typically, the emission face 4 is concave in shape, such as being hemispherical, elliptical, or toroidal in shape. Naturally, the emission face 4 may present a shape other than a concave shape, such as for example a plane shape.

The ultrasound transducer 3 is thus positioned directly facing the opening 5. Typically, the ultrasound transducer 3 is situated at or a little behind the opening 5.

Depending on how the production source 1 of the invention is embodied, this production source 1 is for receiving various pieces of equipment or accessories, each adapted to a specific function.

When the source 1 is used to produce ultrasound, the ultrasound production source 1 includes a flexible membrane 8 placed in front of the emission face 4 and made of a material that is transparent to ultrasound. This flexible membrane 8 co-operates with the emission face 4 to define a confinement chamber 10 for a cooling fluid that is also suitable for performing an acoustic coupling function with the medium that is to be insonified. Typically, the cooling fluid is a liquid based on water that has previously been degassed in order to improve wave propagation, or oil selected from oils presenting acoustic characteristics of low ultrasound absorption. It is also possible to use the liquid described in patent EP 1 038 551.

The confinement chamber 10 includes at least one inlet for the cooling fluid, which is delivered via at least one feed pipe 11. The confinement chamber 10 also has at least one outlet communicating with an outlet pipe 12 thus enabling the fluid to flow inside the confinement chamber.

The flexible membrane 8 is made of any suitable material such as silicone or latex or polyurethane or any material presenting low acoustic absorption so as to reduce acoustic energy losses associated with heating of the membrane.

The flexible membrane 8 is mounted on the body 2 by a fastener system 14 that is both leaktight and also removable or separable. The fastener system 14 makes it possible, at will to change the flexible membrane 8 quickly and easily, with the confinement chamber 10 being sealed once more after the membrane has been changed.

In accordance with the invention, the fastener system 14 comprises a fastener ring 15 for assembling onto the body 2 in separable manner. The fastener ring 15 and the body 2 are provided with a screw thread assembly system 16, 17 serving to hold the flexible membrane 8 pressed in sealed manner against the body 2 by screwing the fastener ring 15 onto the body 2.

Figure 2:
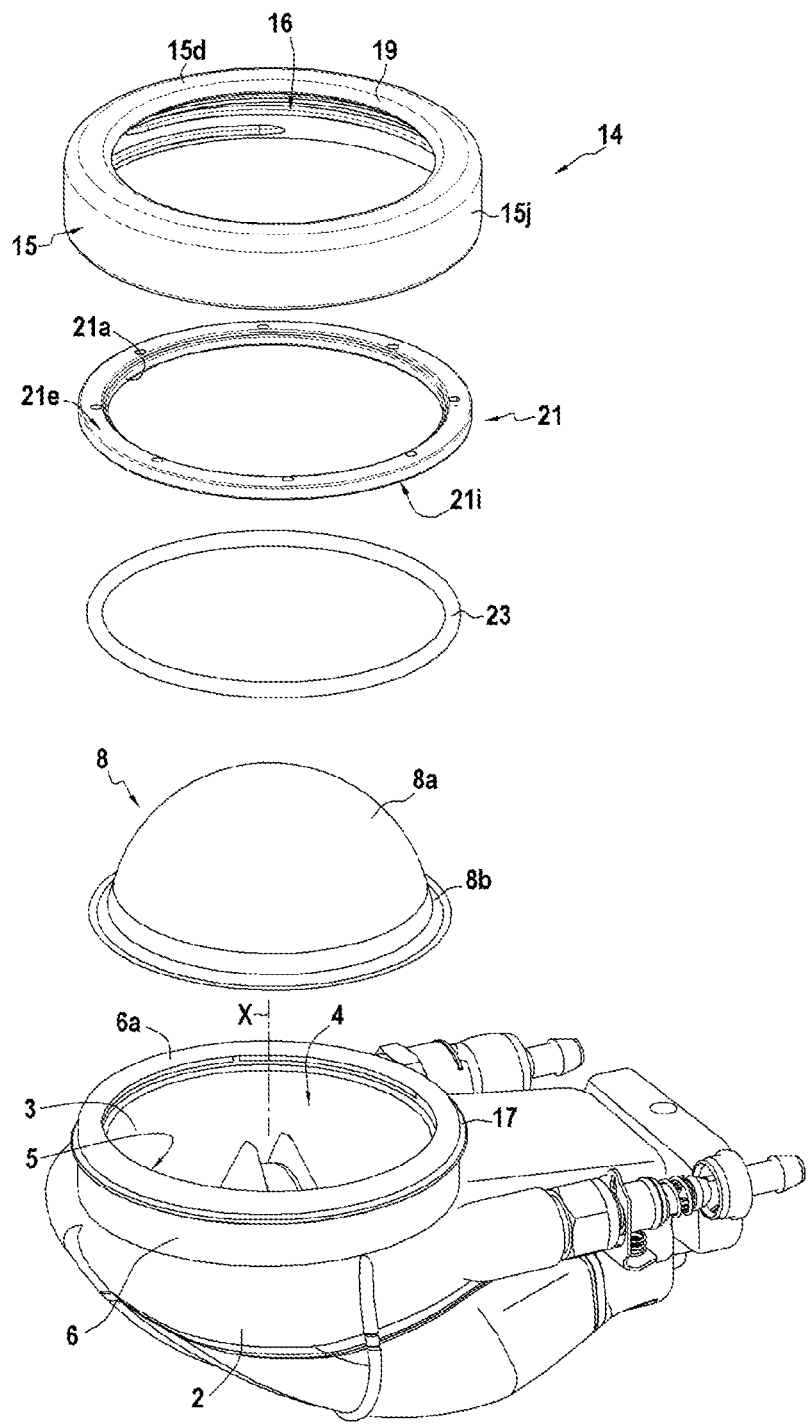
FIG. 2 is an exploded perspective view of an embodiment of an ultrasound production source in accordance with the invention.
Figure 3:
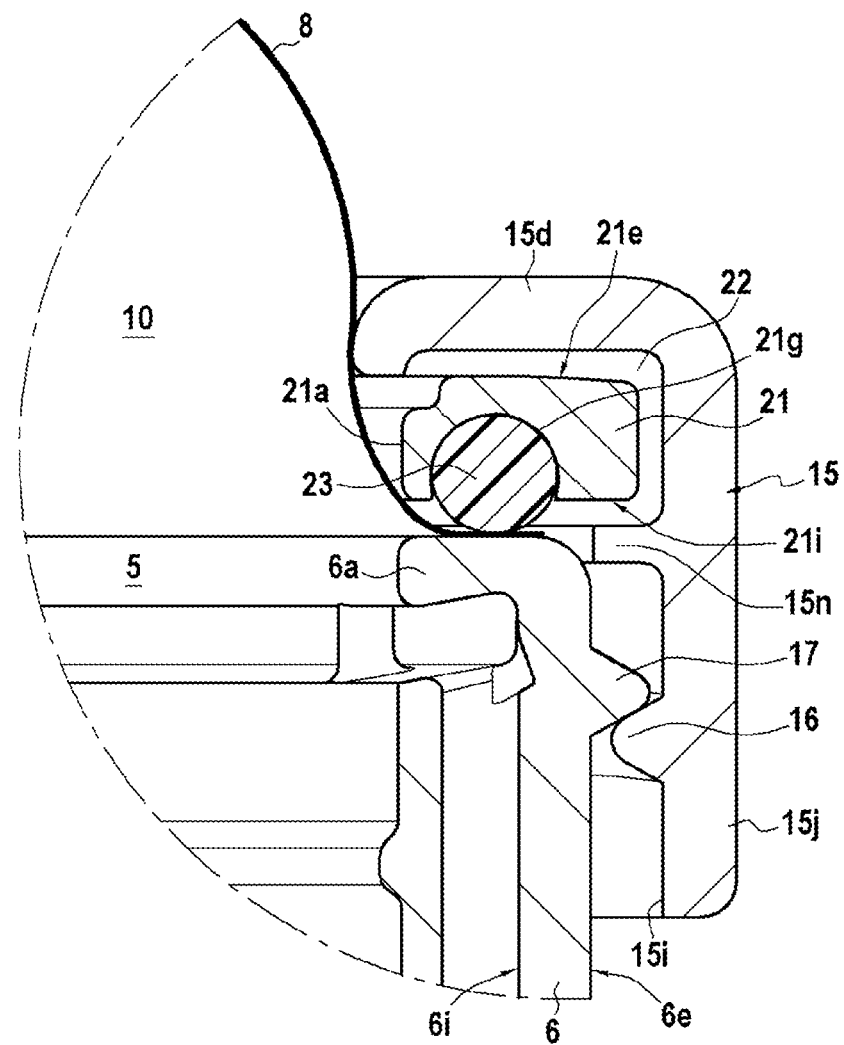
FIG. 3 is an elevation view in section on plane III of the ultrasound production source shown in FIG. 1.

As can be seen more particularly in FIGS. 2 and 3, the fastener ring 15 is in the form of an annular body having an annular top wall 15*d* defining in its center a central passage 19 for a portion of the flexible membrane 8, and in particular a central portion 8*a* of the flexible membrane. The flexible membrane 8 and the fastener ring 15 are two parts that are independent of each other. Typically, the central passage 19 presents a section corresponding substantially to the section of the opening 5 so that when the fastener ring 15 is mounted in position on the body 2, the opening 5 and the central passage 19 coincide.

Typically, the central passage 19 presents a circular outline. Naturally, the flexible membrane 8 is of a shape that is adapted or deformable so as to enable its central portion 8*a* to pass through the central passage 19, and thus form the confinement chamber 10. The central portion 8*a* of the flexible membrane is bordered by a peripheral portion 8*b* that is to co-operate with the body 2 in order to seal the confinement chamber 10. More precisely, the peripheral portion 8*b* of the flexible membrane 8 is adapted to press against the annular rim 6*a* of the tubular wall 6.

The top annular wall 15*d* is extended at right angles by a tubular skirt 15*j* presenting an inside face 15*i* and designed to extend facing the tubular wall 6 of the body 2 when the fastener ring 15 is mounted in position on the body 2.

Figure 4:
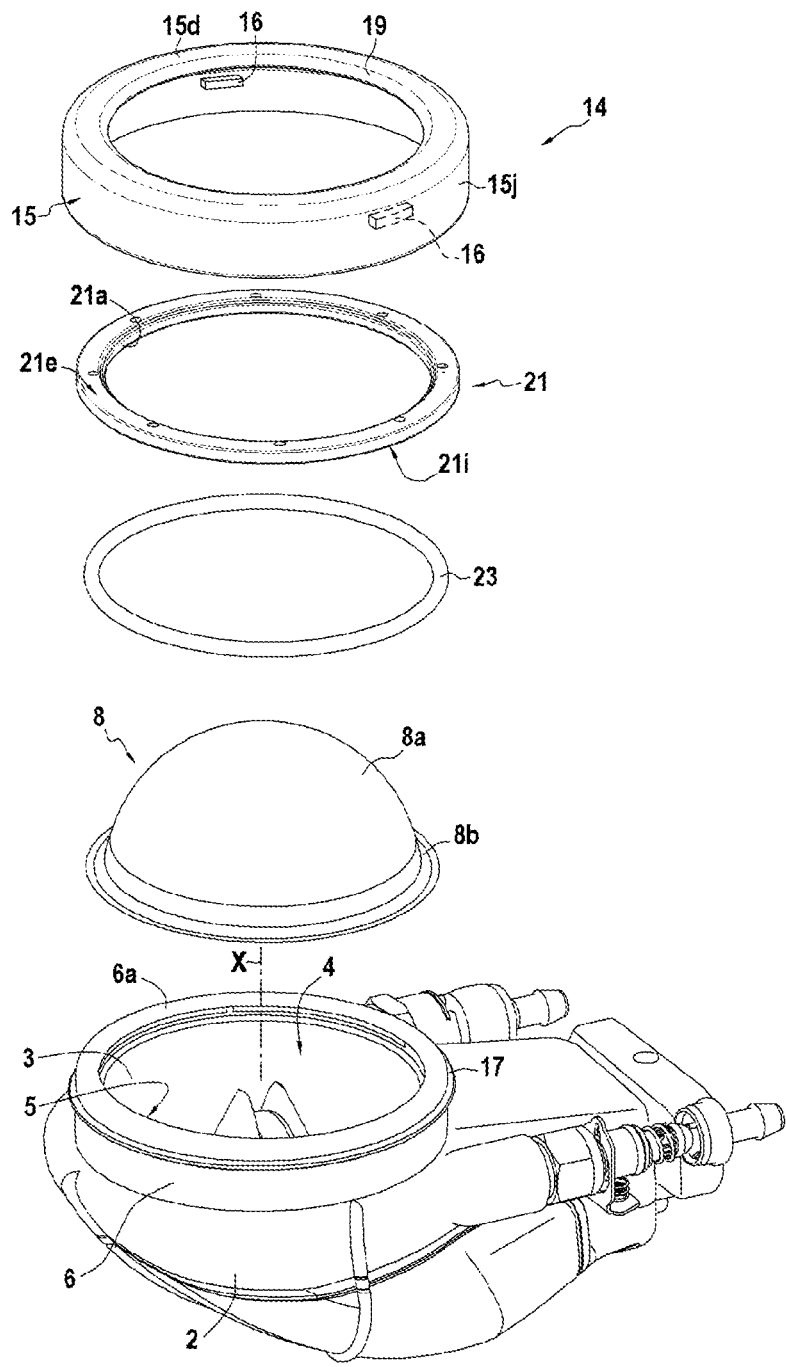
FIG. 4 is a perspective view showing another embodiment of an ultrasound production source in accordance with the invention.

The screw thread assembly system 16, 17 between the fastener ring 15 and the body 2 may be made in any appropriate manner. Such a screw thread assembly system comprises at least one helical rib or thread 17 co-operating with at least one complementary helical rib or thread 16. The thread 17 is provided on the fastener ring 15 or on the body 2, while the complementary thread 16 is provided respectively on the body 2 or the fastener ring 15. It should be observed that the thread 17 or the complementary thread 16 may be made in the form of a continuous element (FIG. 2) or in the form of discontinuous elements such as studs or tabs (FIG. 4). Likewise, the screw thread assembly system 16, 17 may comprise a plurality of helical threads 17 and a plurality of complementary helical threads 16.

In the embodiment shown in FIG. 3, the body 2 and in particular the tubular wall 6, presents externally at least one thread 17, while the fastener ring 15 is provided with a complementary thread 16 such as tapping. In the example shown in FIG. 4, the fastener ring 15 is provided with two studs 16 acting as the complementary thread 16 and co-operating with the thread 17 in order to screw the ring onto the body. It should be observed that provision may be made for the studs on the outside surface of the body 2 and in particular on the tubular wall 6 to act as the thread 17 so that they co-operate with at least one complementary thread 16 of the fastener ring 15.

When the fastener ring 15 is mounted in position on the body 2, the peripheral portion 8*b* of the flexible membrane 8 is interposed between the fastener ring 15 and the body 2, and more particularly the tubular wall 6. Screwing the fastener ring 15 onto the body 2 serves to hold the flexible membrane 8 pressed in sealed manner against the body 2. For example, the flexible membrane 8 is of dimensions such that its peripheral portion 8*b* is positioned away from the thread 17.

According to an advantageous embodiment characteristic, the fastener ring 15 has a washer 21 mounted to turn freely relative to the fastener ring 15. The washer 21 presents a through hole 21*a* in its central portion for passing the central portion 8*a* of the flexible membrane. The section of the through hole 21*a* corresponds substantially to the section of the central passage 19 in the top annular wall 15*d* or, as in the example shown, it is greater than that section of the central passage 19 in the top annular wall 15*d*. When the washer 21 is in the mounted position, its inside edge is set back from the inside edge of the annular top wall 15*d* of the fastener ring 15.

This washer 21, which includes a top annular face 21*e* and a bottom annular face 21*i*, is held in the fastener ring 15 inside an annular recess 22 defined by the inside face of the top annular wall 15*d* and by a rib 15*n* projecting from the inside face 15*i* of the skirt 15*j*. The recess 22 thus presents a C-shaped section. The freedom of the washer 21 to move transversely is limited on one side by the bottom face of the top annular wall 15*d* against which the top annular face 21*e* can come into contact, and on the other side by the rib 15*n* against which the bottom annular face 21*i* can come into contact. The freedom of the washer 21 to move radially is limited by the inside face 15*i* of the skirt 15*j*. It should be observed that the rib 15*n* may be constituted by the complementary thread 16. Thus, the washer 21 and the fastener ring 15 are connected together while being free to pivot relative to each other about the axis of symmetry of the washer.

According to an advantageous embodiment characteristic, the washer 21 is made of a material having very great non-stick capability, e.g. such as polytetrafluoroethylene (PTFE or Teflon).

The washer 21 and the fastener ring 15 may be assembled together in any appropriate manner. One solution consists in using a known three-dimensional printing technique to make the fastener ring 15 incorporating the washer 21. The washer 21 may also be put into place by being deformed inside the fastener ring 15.

It should be understood that when the fastener ring 15 is not in its mounted position on the body 2, the washer 21 is free to turn relative to the fastener ring 15. In other words, the fastener ring 15 can be turned without turning the washer 21, which remains stationary.

Prior to putting the fastener ring 15 into place, it should be observed that the flexible membrane 8 is put into position so that its peripheral portion 8*b* covers the annular rim 6*a*. When the fastener ring 15 is mounted on the body 2, the washer 21 is not yet in contact with the peripheral portion 8*b* of the flexible membrane 8, which is itself in contact only with the annular rim 6*a* of the tubular wall 6. On turning the fastener ring 15, both the ring and the washer 21 turn together. When the washer 21 becomes positioned so as to come into contact with the peripheral portion 8*b*, the flexible membrane 8 is then interposed between the washer 21 and the annular rim 6*a* of the tubular wall 6. The fastener ring 15 continues to turn, while the washer 21 is held stationary relative to the annular rim 6*a* of the tubular wall 6 and relative to the flexible membrane 8.

During the operation of assembling the fastener ring 15 on the body 2, the fastener ring 15 is turned without causing the washer 21 to turn, which washer thus holds the flexible membrane 8 in place without creasing it. At the end of being tightened, the fastener ring 15 acts via its top annular wall 15d to exert a bearing force on the top annular face 21e so as to block the washer 21 in position, thereby pressing the flexible membrane 8 against the annular rim 6a of the tubular wall 6.

The washer 21 is mounted in the fastener ring 15 with limited freedom to move laterally so as to exert a pressure force on the membrane when the fastener ring 15 is screwed on the body 2. In other words, the washer 21 is taken to its final pressing position while the fastener ring 15 is being tightened by virtue of the bottom face of the top annular wall 15d coming to bear against the top annular face 21e of the washer. The screw fastening stroke of the fastener ring 15 naturally depends on the pitch of the thread 17 and on the clearance between the bottom face of the top annular wall 15d and the top annular face 21e of the washer. The lateral movement associated with the above-described radial movement serves to provide a space into which cleaning and decontamination liquid can penetrate and perform their functions during stages of decontamination and sterilization.

It should be observed that the washer 21 may come directly into contact with the flexible membrane 8, or else, as in the example shown, it may come into contact therewith via a plane or annular sealing gasket 23 that bears against the flexible membrane 8 that is bearing against the annular rim 6a. In a preferred embodiment example, the sealing gasket 23 is mounted on the washer 21. As seen in FIG. 3, the washer 21 has a mounting groove 21g in its bottom annular face 21i in which the sealing gasket 23 is mounted.

Figure 5:
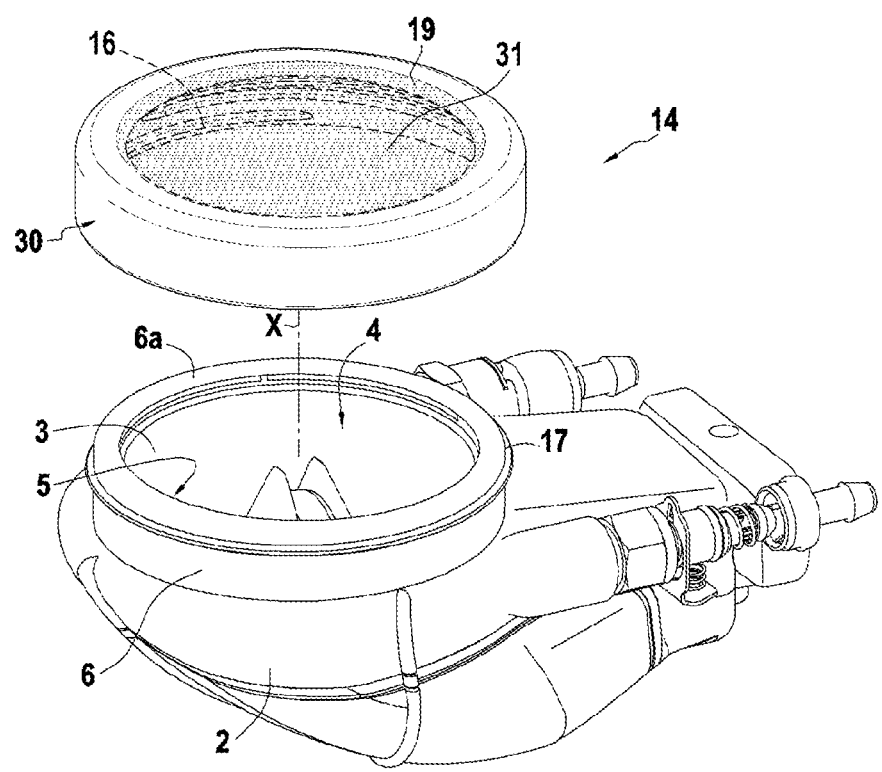
FIG. 5 is an exploded perspective view showing an embodiment of an ultrasound production source in accordance with the invention for fitting with a protective cover.

When the source 1 is not being used for producing ultrasound, the fastener ring 15 can be removed. In the absence of the fastener ring 15, the body 2 can receive a protective cover 30 for protecting the ultrasound transducer 3. As shown in FIG. 5, the body 2 includes the thread 17 or the complementary thread 16 that, in the absence of the fastener ring 15, co-operates respectively with a complementary thread 16 or a thread 17 of the protective cover 30. The protective cover 30 is similar in design to the fastener ring 15, but it also includes a closure wall 31 that closes the central passage 19 of the fastener ring 15. The protective cover 30 is thus screwed onto the tubular wall 6 of the body 2, thereby protecting the ultrasound transducer 3, while it is not in use.

In the absence of the fastener ring 15 and of the protective cover 30, the body 2 is in a position to receive an alignment system suitable for use in particular during a calibration step. During a calibration step, a ring 35 is used that is analogous to the fastener ring 15 and that is fitted with an alignment system 36. For example, the alignment system 36 has an arm 37 carried by the ring and fitted at its end with a sensor 38 for measuring the acoustic pressure generated by the transducer or for visualizing the ultrasound propagation axis X or the focus zone of the ultrasound transducer 3. The body 2 includes the thread 17 or the complementary thread 16 that, in the absence of the fastener ring 15 and of the protective cover 30, co-operates respectively with a complementary thread 16 or a thread 17 of the ring 35 fitted with the alignment system 36. The resulting mechanical connection with the body 2, and consequently with the ultrasound transducer 3, makes it possible to align the sensor 38 on the acoustic axis X or the focus zone of the emission face 4 in order to measure pressure on the acoustic axis X or to give its position or to give the position of the focus zone.

It can be seen from the above description that, depending on the use being made of the ultrasound production source 1, the source and in particular the tubular wall 6 of its body, is adapted to use screw fastening for mounting either a fastener ring 15 for fastening the flexible membrane 8, or a protective cover 30, or a ring 35 fitted with an alignment system 36. The operations of mounting and of removing are particularly simple to carry though without any risk of deteriorating the ultrasound transducer 3.

The invention thus proposes an assembly for producing ultrasound that comprises a production source 1 in accordance with the invention and, as accessories, a fastener ring 15 for fastening a flexible membrane, a protective cover 30, and/or a ring 35 fitted with an alignment system 36, each of the accessories having a complementary thread 16 co-operating with the thread 17 of the tubular wall 6 of the body of the production source.

The invention is not limited to the examples described and shown since various modifications can be made thereto without going beyond its ambit.

The invention claimed is:

1. An ultrasound production source device comprising:
a body having an ultrasound transducer disposed therein, said body comprising an externally threaded tubular wall, and a peripheral annular rim defining an opening;
wherein an emission face of the ultrasound transducer is configured to face the opening of the body;
a flexible membrane comprising a peripheral portion having an upper surface and a lower surface;
an internally threaded fastener ring having a top annular wall defining an opening, and a skirt extending peripherally from the top annular wall;
wherein a thread of the fastener ring is complementary to a thread of the body;
wherein the fastener ring comprises an annular recess defined by an inner face of the annular wall and a rib projecting from an inner face of the skirt;
a washer retained within the annular recess; said washer having an upper annular face and a lower annular face defining an opening;
wherein, in an unassembled state of the device:
a transverse movement of the washer retained within the annular recess is limited, on the upper annular face, by the inner face of the annular wall, and on the lower annular face, by the rib;
a radial movement of the washer retained within the annular recess is limited by the inner face of the skirt; and the washer and the fastener ring are pivotable relative to each other about a common axis of symmetry; and
the thickness of the washer is less than the height of the annular recess defined between the inner face of the annular wall and the rib, so that the washer is movable transversely between the inner face of the annular wall and the rib and the washer outer diameter is larger than the inner through diameter of the rib, and
wherein, in an assembled state of the device:
the lower surface of the peripheral portion of the flexible membrane sealingly engages the annular rim of the body;
the lower annular face of the washer sealingly engages the upper surface of the peripheral portion of the flexible membrane;
the upper annular face of the washer sealingly engages the inner face of the annular wall of the fastener ring;
a portion of the flexible membrane extends through the opening of the washer and the opening of the fastener ring;

the fastener ring is threadingly connected to the body to sealingly engage the flexible membrane against the body.

2. The device according to claim 1, wherein the annular recess has a C-shaped section.

3. The device according to claim 1, wherein the washer is fitted with a sealing gasket in contact with the flexible membrane.

4. The device according to claim 1, wherein the washer is made of polytetrafluoroethylene.

5. The device according to claim 1, wherein the thread of the fastener ring, or the thread of the thread of the body, is made in a form of a continuous element, or a discontinuous element.

6. The device according to claim 1, wherein the thread of the body co-operates with a complementary thread of a protective cover.

7. The device according to claim 1, wherein the thread of the body co-operates with a complementary thread of a ring fitted with an alignment system suitable for use during a calibration step.

8. An ultrasound production assembly comprising the ultrasound production source device of claim 1 and the following accessories: a fastener ring for fastening a flexible membrane; a protective cover; and a ring fitted with an alignment system; each of the accessories including a complementary thread co-operating with the thread of the tubular wall of the body of the ultrasound production source.

9. The device according to claim 1, wherein the fastener ring comprises a central passage that receives a portion of the flexible membrane in the assembled state of the device.

* * * * *